United States Patent [19]
Williams et al.

[11] Patent Number: 5,679,573
[45] Date of Patent: Oct. 21, 1997

[54] STABILIZED AQUEOUS STEROID IMMUNOASSAY STANDARDS WITH CYCLODEXTRINS

[75] Inventors: Gregg T. Williams, Villa Park; William R. Groskopf, Libertyville; Beimar N. Iriarte, Buffalo Grove, all of Ill.; Lester A. Mitscher, Lawrence, Kans.

[73] Assignee: Abbott Laboratories, Abbott Park, Ill.

[21] Appl. No.: 507,958

[22] Filed: Jul. 27, 1995

[51] Int. Cl.$^6$ ........................................... G01N 31/00
[52] U.S. Cl. ........................... 436/8; 436/16; 436/18
[58] Field of Search .................... 436/8, 16, 18; 514/58; 435/240.31

[56] References Cited

U.S. PATENT DOCUMENTS

| | | | |
|---|---|---|---|
| 4,383,992 | 5/1983 | Lipari | 424/238 |
| 4,596,795 | 6/1986 | Pitha | 514/58 |
| 4,647,532 | 3/1987 | Wanatabe et al. | 435/28 |
| 4,727,064 | 2/1988 | Pitha | 514/58 |
| 4,764,604 | 8/1988 | Muller | 514/58 |
| 4,870,060 | 9/1989 | Muller | 514/58 |
| 4,877,774 | 10/1989 | Pitha et al. | 514/58 |
| 4,883,785 | 11/1989 | Chow et al. | 514/58 |
| 4,956,274 | 9/1990 | Uhanna et al. | 435/7 |
| 5,024,998 | 6/1991 | Bodor | 514/58 |
| 5,068,227 | 11/1991 | Weinshenker | 514/58 |
| 5,182,270 | 1/1993 | Musson et al. | 514/58 |
| 5,229,370 | 7/1993 | Ammeraal | 514/26 |
| 5,324,718 | 6/1994 | Loftsson | 514/58 |
| 5,324,750 | 6/1994 | Lincoln et al. | 514/510 |
| 5,328,846 | 7/1994 | Moore | 435/240.31 |
| 5,376,641 | 12/1994 | Ammeraal | 514/26 |

FOREIGN PATENT DOCUMENTS

| | | |
|---|---|---|
| 0349091 | 1/1990 | European Pat. Off. |
| 63-12025 | 5/1988 | Japan. |
| 9105605 | 2/1991 | WIPO. |

OTHER PUBLICATIONS

Albers, E. et al., Complexation of Steroid Hormones with Cyclodextrin Derivatives:, *Journal of Pharmaceutical Sciences*, vol. 81, No. 8, Aug. 1992, pp. 756–761.

Poudrier, J. K., Corn Meets Nanotechnology and They're Getting Along "Amazingly" Well, *Today's Chemist at Work*, Feb. 1995, pp. 25–30.

*Primary Examiner*—Jill Warden
*Assistant Examiner*—Alexander Markoff
*Attorney, Agent, or Firm*—Lawrence S. Pope

[57] ABSTRACT

Aqueous solutions of steroid compounds which have biological activity and have a tendency to oxidative degradation at temperatures between 2° and 8° C. on storage in excess of several months are stabilized by the addition of cyclodextrin.

20 Claims, 9 Drawing Sheets

1

STABILIZED AQUEOUS STEROID IMMUNOASSAY STANDARDS WITH CYCLODEXTRINS

FIELD OF THE INVENTION

Steroid compounds, and in particular biologically active steroid compounds susceptible to degradation by oxygen in aqueous protein containing media are given enhanced storage stability by the addition of cyclodextrins.

BACKGROUND OF THE INVENTION

A widely employed method of analyzing biological fluids, for example the bodily fluids of human beings for the presence or amount of both naturally occurring and synthetic biologically active compounds is by immunoassay. The interaction between the analyte of interest and an antibody which recognizes this analyte is measured. This often provides a relatively fast and inexpensive method of quantitating the amount of a given analyte. The analyte antibody reaction may be measured in a wide variety of techniques. One technique is the competitive assay in which an anti-analyte antibody is immobilized on a solid phase and then reacted with both a known amount of a labeled analyte and a sample suspected of containing analyte. The analyte in the sample then competes with the labeled analyte for binding to the immobilized antibody. The amount of label captured by immobilized antibody is then related, for example in some type of inverse manner, to the amount of analyte present in the sample.

All analytical techniques require some reference to a standard but such reference is particularly important for immunoassays. The reagents utilized in such assays include biological materials whose reactivity is not exactly reproducible but reproducible only within a given range. In addition the immunological binding between an antibody and its analyte may be influenced by subtle factors which cannot always be controlled. In this regard too rigorous attempts to obtain precise reproducibility are inconsistent with the goal of a fast and inexpensive assay.

Therefore, the practice has developed of providing one or more standards to be included with each run of an immunoassay. For instance the IM$_x$® instrument manufactured by Abbott Laboratories can analyze in excess of twenty samples per run. It is typical to include several samples having a known amount of analyte in each run to provide a measure of the variability. Such standard samples are commonly known as controls.

In addition it is also typical to provide a number of samples having known amounts of analyte in order to calibrate and from time to time recalibrate the analyzer. Such standard samples are commonly referred to as calibrators.

For both calibrators and controls it has been desirable to use a diluent which displays a behavior in the assay similar to that of the bodily fluid which is to be assayed for analyte. For instance, if human serum is to be analyzed, the calibrators and controls may both be prepared with appropriately treated normal human serum. Alternatively an aqueous medium having a protein content similar to serum, for instance a buffered solution of bovine serum albumin (BSA) may be used.

A class of analytes of interest, the steroids, display a tendency to degrade over time in such buffered aqueous protein containing media. This tendency has been observed both in charcoal stripped human serum and in aqueous solutions of BSA. In this regard, human serum intended for use as a calibrator or control matrix or carrier is charcoal stripped to remove any endogenous steroid which might be present. Thus the initial steroid content can be precisely controlled by simply adding a measured amount to the stripped serum.

However, the process of charcoal stripping introduces additional metal ions into the matrix which catalyze the destruction of the analyte. The charcoal can be extremely difficult to remove, and may require several filtrations for its removal. Many of the preps have a very poor yield. The resulting matrix is often extremely expensive, somewhat unpredictable with respect to analyte stability, biohazardous, and subject to frequent availability issues.

The only other method demonstrated to improve the stability of steroids in calibrators has been freezing. This method unfortunately raises customer convenience and assay performance issues resulting from particulates that form upon thawing (often called shedding).

Thus there is a need for calibrator and control solutions for steroid immunoassays which display extended storage stability under normal field conditions. In particular there is a need for such solutions which do not degrade significantly when stored for extended periods at temperatures between about 2° and 8° C. It is particularly desirable for such solutions to be stable for in excess of six months.

Another issue pertaining to immunoassays is that of recovery of the analyte. Recovery is typically defined as equal to observed concentration/actual concentration X 100%. Unfortunately, buffered protein-free solutions containing steroids typically display over-recovery data, often times equal to as much as 200% or more. Because of this there has been a reluctance to move away from protein containing matrices. Thus, there is also a need in the art for stabilized control solutions for steroids used in immunoassays which additionally exhibit acceptable recovery data, and particularly, a recovery equal to about 100%.

OBJECTS OF THE INVENTION

It is therefore an object of the present invention to provide for the long term storage and stability of steroids which are utilized in immunoassays.

Another object of the invention is to employ cyclodextrin in a calibrator and control solution for steroid immunoassays.

A further object of the invention is the stabilization of biologically active steroid compounds using cyclodextrin.

Another object is to provide for calibrator and control solutions for steroid immunoassays which will exhibit storage stability for several months at temperatures in the range of about 2° to 8° C.

Still another object of the invention is to provide a means for the long-term storage of steroids for use in immunoassays utilizing components which do not adversely affect the recovery data for the steroid.

BRIEF DESCRIPTION OF THE INVENTION

Steroid compounds are made more storage stable by the addition of cyclodextrins. Especially preferred as part of the invention are biologically active steroid compounds which are susceptible to degradation by oxidation in aqueous solutions and which are suitable for the standardization of immunoassays of human bodily fluids. The steroids of particular interest include, for example, the naturally occurring hormonal steroids such as estradiol and progesterone. The aqueous media of interest may be buffered to a pH between about 6 and 9. The solutions of particular interest include those with a steroid concentration between about $2.5 \times 10^{-11}$ and $1.0 \times 10^{-7}$ g/mL and a cyclodextrin concentration of greater than about 0.1 mM, preferably between about 0.2 and 25 mM.

Recovery data for immunoassays using steroid calibrator and control solutions stabilized with cyclodextrins are also excellent.

DETAILED DESCRIPTION OF THE INVENTION

Figure 1:
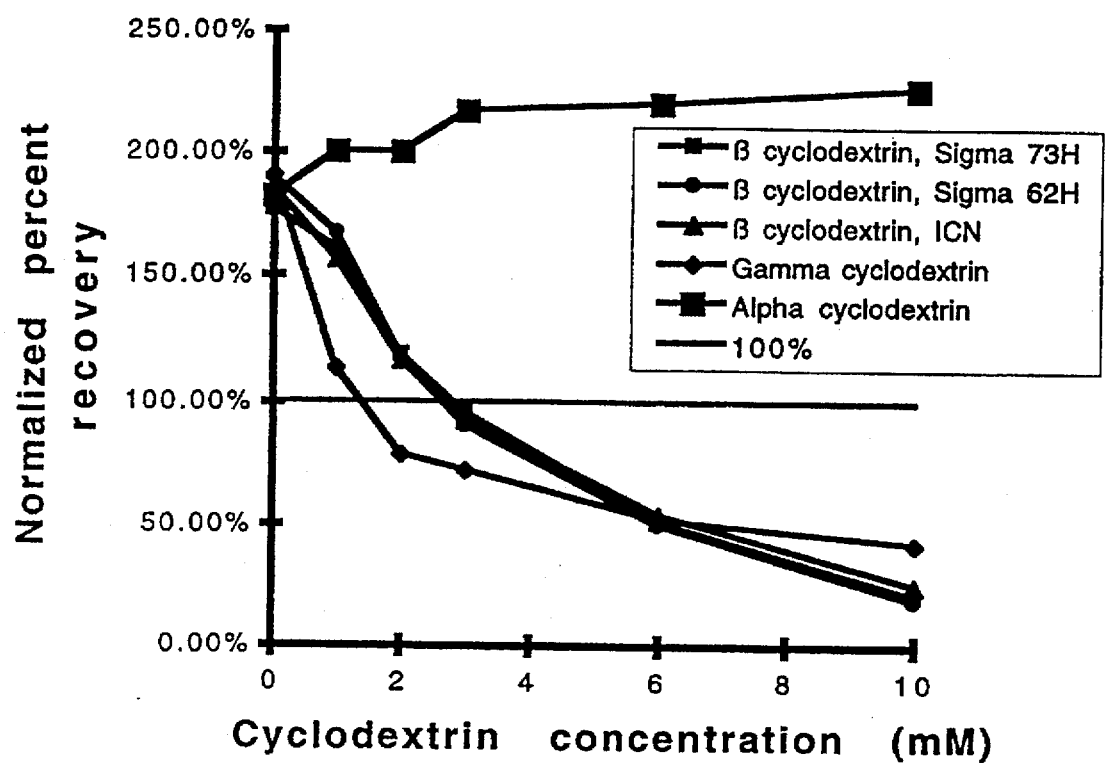
FIG. 1 is a graph of the Effects of Alpha, Beta and Gamma Cyclodextrins on Progesterone Recovery.

The steroids suitable for use with the invention are any one or more of the numerous naturally occuring, fat-soluble organic compounds having a 17-carbon atom ring as a basis, and including, for example, the sterols, and bile acids, many hormones, certain natural drugs such as digitalis compounds and the precursors of certain vitamins.

Of particular interest with regard to the present invention are those steroids which display biological activity in humans and have a tendency to undergo oxidative degradation in an aqueous medium such as biological fluid. These steroids are likely targets for immunoassay and consequently are likely to be utilized as standards for such assays. Such standards typically utilize aqueous media in order to present the reference steroid to the assay in a medium similar to a biological fluid, for example bodily fluid, on which the immunoassay is being conducted. Among these steroids are the naturally occurring hormonal steroids and those of particular interest are those whose normal biological levels fluctuate such as the female sex hormones. Included within this group are progesterone, estrone and estradiol. Other steroids of interest include cortisol and testosterone. Still other steroids for use in immunoassays may be contemplated by those skilled in the art and are therefore within the scope of the invention.

The cyclodextrins, as by-products of corn, are highly preferred for stabilizing the aforementioned steroids under aqueous conditions suitable for immunoassay. Especially preferred are the Beta-, Gamma- and modified Beta-cyclodextrins. Those skilled in the art will recognize that modified Beta-cyclodextrin is 2-hydroxy-propyl Beta-cyclodextrin. Of the aforesaid compounds, Beta-cyclodextrin is particularly desirable.

The ring structure of the cyclodextrins in general, and the β- cyclodextrin molecule in particular, imparts properties that are different from those of non-cyclic carbohydrates in a similar molecular weight range, including stability in hot basic solutions, resistance to hydrolysis by most organic acids and some alpha amylases, complete resistance to yeast fermentation and beta amylase hydrolysis, and a remarkably high decomposition temperature of 300° C. The molecular arrangement and the properties associated with that arrangement give the aforesaid cyclodextrins, and particularly β-cyclodextrin, a unique property: the ability to form inclusion complexes, trapping guest molecules within themselves, protecting them and even altering some of their properties. The hydrophobic interior of β-cyclodextrin, for example, is such that the steroid molecules can enter for complexation without changing their actual structure. Thus, the β-cyclodextrin molecule provides a long-term storage mechanism for the steroids, and when ready to be utilized in immunoassays, the steroids emerge with their physical structure intact. This is perhaps one reason why β-cyclodextrin is a particularly preferred cyclodextrin for use in the invention.

It is highly preferred that the cyclodextrins as part of the invention be included in aqueous media, and in particular, in those aqueous media which are substantially free of protein content. While it may often be desirable for the standards for an immunoassay to be carried in a medium which is similar to or mimics the behavior of a human bodily fluid such as a serum, in some cases it is necesary to use protein contents dramatically different than that of the human bodily fluid to be assayed. This may allow adjustment for other characteristics of the bodily fluid.

It is preferred that the aqueous medium be substantially free of fibrinogen. Thus it is more desirable to use media other than plasma. In this regard it is also preferred to avoid media which contain particulate forming components.

In those somewhat less preferred embodiments wherein a protein-based media is utilized, it is desirable that the protein concentration range from between about 10 and 300 mg/mL or about 1 to 30%, with about 50 mg/mL being typical for serum. A concentration range of about 2.5 to 25% is more preferred, with about 2.5 to 5% being especially desirable. This protein content may be naturally present, for instance in normal human serum, or may be added such as a five percent weight per volume aqueous solution of bovine serum albumin (BSA). Commercially available preparations such as Plasma Diagnostic Base (PDB), which is then charcoal stripped, can also be used, as well as Sera Sub (™).

It is preferred that any protein solution be essentially free of endogenous steroid. Thus if the protein solution must be normal human serum it is most preferably charcoal stripped to remove the naturally occurring steroids. On the other hand, protein preparations from which the steroids have been removed by other techniques such as commercially available steroid free non-charcoal stripped BSA may in some instances be used. Among these are those obtained by a wash with an organic phase. It is felt that charcoal stripping may contribute undesirable transition metals such as iron. It is felt that the protein itself may often be a source of undesirable transition metals. Proteins are known to complex with metals in ways which make it difficult to obtain transition metal free protein.

It is preferred although not necessary that the aqueous medium have a pH similar to that of human bodily fluids. It is particularly desirable that the aqueous medium have a pH between about 6 and 9 with a pH between 7 and 8.5 being especially preferred. The pH of the aqueous medium is conveniently adjusted with any of the common buffers utilized with biological materials such as tris (hydroxymethly) aminomethane commonly known as TRIS. As an example, a 0.1M concentration of TRIS may be utilized. Other buffers may be available to those skilled in the art, along with concentration ranges not heretofore specifically set forth.

The steroid concentrations of the aqueous solutions of interest should span the range of steroid concentrations encountered in assaying human bodily fluids. Typically various steroids are assayed for at levels between about 5 picograms per mL and 100 nanograms per mL. Of particular interest are concentrations between about $5 \times 10^{-11}$ and $4 \times 10^{-8}$ gram per mL.

The cyclodextrins as part of the invention should be utilized in amounts effective to inhibit the oxidative degradation of the aqueous steroid solutions. It is preferred to utilize them in amounts in excess of about 0.1 mM and it is particularly preferred to use them in amounts between about 0.2 and 25 mM. It is particularly advantageous to utilize a cyclodextrin concentration of at least about 1 mM. There appears to be a limited advantage in utilizing cyclodextrin concentrations in excess of about 25 mM. However, other than the cost there does not appear to be much disadvantage in using higher concentrations.

An especially preferred concentration of cyclodextrin for use in the invention would be in the range of about 2 mM to 6 mM, preferably about 2.5 mM to 5 mM. In many embodiments, it is especially desirable to utilize about 2.4 mM to about 2.7 mM of cyclodextrin to stabilize steroid formulations. The aforesaid concentrations are very often steroid specific, and therefore those skilled in the art may find other concentrations that best suit their own particular requirements, and may vary somewhat depending upon the particular steroid utilized. Very often, a highly desirable quantity of cyclodextrin to be utilized is one which will permit a 100% recovery for the steroid, as further discussed herein.

The concentration of cyclodextrin utilized as part of the invention should not compromise the recovery data of the particular steroid at issue in immunoassays. It is extremely desirable that there be a recovery of about 100% for the steroid, based upon the particular concentration of cyclodextrin which is utilized in the corresponding calibrator solution. Beta- and Gamma- cyclodextrins permit 100% recovery of the steroid, and therefore further alleviate the need for a protein-containing matrix to store the steroid. Since protein contributes to the breakdown of the steroid, there is a distinct advantage in often times not utilizing this medium. However, protein-based media can in many instances can still display acceptable or even excellent recovery data.

The inhibition of oxidative degradation achieved by the cyclodextrins, and particularly by β-cyclodextrin, may be conveniently assessed by stressing aqueous steroid solutions at elevated temperatures for various times and observing the loss of steroid content detectable by immunoassay. The results obtained by elevated temperature testing are predictive of the longer term stability of steroid solutions held at lower temperatures.

Steroid standards for immunoassays are typically maintained at temperatures between about 2° and 8° C. and desirably have stabilities in excess of about six months, i.e. do not display significant degradation within six months. It is particularly desirable that the standards display a loss of signal in an immunoassay of less than about 10 percent preferably less than about 5 percent, and even more desirably less than about 1 percent.

Such stabilities can be conveniently projected from heat aging at about 37° C. and higher over the course of between, for example, 2 to 5 weeks. Compositions which display less than about 10% loss for four weeks are expected to have stabilities in excess of about six months. Similar results may be expected for compositions showing well under about 5% loss after approximately 2.5 weeks.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

IMx® Estradiol Assay

Estradiol assays were performed with the following format on Abbott Laboratories IMx® disposable cartridges by an IMx® instrument. Seventy five microliters (75 µL) of a serum sample were mixed with 35 µL of 5alphadihydrotestosterone (DHT) buffer, 50 µL of anti-estradiol antibody coated microparticles and 90 µL of IMx® Buffer. The reaction mixture was incubated for 27.5 minutes at 35 ° C. DHT buffer was composed of 2 µg/mL of 5-alphadihydrotestosterone, 0.75% (w/v) saponin, 0.5M glycine, 0.25 mM sodium citrate and 0.12% methyl isothiazolinone, all at pH 4.5. Anti-estradiol antibody coated microparticles (0.005–0.02% solids) were suspended in microparticle buffer which was composed of 0.1M bis-(2-hydroxyethyl)iminotris(hydroxymethyl)methane (Bis-Tris), 0.1M sodium chloride, 13.6% sucrose, 0.1% sodium azide and 0.2 mg/mL normal rabbit IgG, all at pH 6.5. IMx® Buffer was composed of 0.3M NaCl, 0.1M TRIS (tris (hydroxymethyl)aminomethane), 0.1% sodium azide, all at pH 7.5. IMx® Estradiol reagents (including DHT buffer, rabbit anti-estradiol antibody coated microparticles, estrogen conjugate and methylumbelliferone phosphate substrate), IMx® Buffer, IMx® disposable cartridges, and IMx® instruments are available commercially from Abbott Laboratories, Abbott Park, Ill. and are described in U.S. Pat. No. 5,342,760, EP-A-288 793 and in Fiore et al., Clin. Chem. 34/9:1726–1732, 1988, all of which are incorporated herein by reference.

One hundred seventy five microliters (175 µL) of the reaction mixture was transferred to the fiber matrix of an IMx® disposable cartridge. The fiber matrix is located over an absorbent pad of the IMx® cartridge. The microparticles were captured by the fiber matrix and the solution was absorbed by the absorbent pad. The microparticles were then washed with IMx® Buffer. Sixty microliters (60 µL) of a steroid-alkaline phosphatase conjugate were added to the matrix, incubated for 12 seconds at 37° C., and then washed again with IMx® Buffer. The conjugate (2–8 µg/ml alkaline phosphatase) was in conjugate buffer composed of 0.1M Bis-Tris, 0.5M sodium chloride, 1% casein, 1mM magnesium chloride, 0.1 mM zinc chloride, 0.1% azide, all at pH 6.5.

Sixty-five microliters (65 µL) of a 1.2 mM solution of 4-methylumbelliferone phosphate in 0.1M 2-amino-2- methyl-1-propanol buffer, pH 9, was added to the matrix and the rate of 4 methylumbelliferone formation was measured by fluorescence reflectance. The IMx® instrument measured fluorescence with a fluorometer that used a mercury arc lamp as its light source (as described in Fiore et al., Clin. Chem. 34/9:1726–1732, 1988, the contents of which are incorporated herein by reference).

EXAMPLE 2

Progesterone Assay on the IMx®

Progesterone assays were performed on IMx® disposable cartridges by an IMx® instrument using a format similar to the estradiol assay in Example 1, with the following modifications.

30 microliters (30 µL) of a serum sample were mixed with 50 µL of an anti-progesterone/alkaline phosphatase conjugate reagent, and 49 µL of IMx® Buffer. The reaction mixture was incubated for 10.2 minutes at 35° C. 51 µl of anti-fluorescein antibody coated microparticle reagent, 50 µl of bihapten reagent, and 3 µL of IMx® Buffer were added to the reaction and the incubation was continued for 10.2 minutes at 35° C. One hundred eighty microliters (180 µL) of the reaction mixture was transferred to the fiber matrix of an IMx® disposable cartridge. The complexes were then washed with IMx® Buffer and left to incubate for 10.2 minutes at 35° C. The addition of 4-methylumbelliferone phosphate and quantification of the rate of 4 methylumbelliferone formation was as described in Example 1.

The anti-progesterone antibody/alkaline phosphatase conjugate reagent was prepared using calf intestine alkaline phosphatase (available from BoeRringer Mannheim, Germany) and a monoclonal anti-progesterone antibody (University of Surrey, England). The phosphatase was modified with iminothiolane (Traut's reagent) and the two proteins were linked with a maleimide/succinimide heterobifunctional linker. The conjugate reagent contains 100 mM TRIS pH 7.5, 500 mM sodium chloride, 0.1% (w/v) sodium azide, 1% (w/v) casein, 1 mM magnesium chloride, 0.1 mM zinc chloride, and 0.5 mg/ml sheep serum. Typical working concentrations of conjugate are approximately 0.3 µg/ml with respect to antibody.

The anti-fluorescein microparticle reagent was prepared using carboxyl-modified latex microparticles (available from Seradyne, Indianapolis, Ind.) and a monoclonal anti fluorescein antibody (Abbott). The antibody was covalently attached to the microparticle using 1-Ethyl-3(3-dimethylaminopropyl) carbodiimide (EDAC). The microparticle reagent contains 150 mM TRIS pH 7.2, 200 mM mM sodium chloride, 13.6% (w/v) sucrose, 0.1% (w/v) sodium azide, 0.1% (v/v) Tween (™) 20, and 0.1 mg/ml mouse IgG. Typical working concentrations of microparticles are approximately 0.02% latex solids.

The bihapten reagent contains progesterone-11 alpha-hemisuccinate-5-(aminoacetamido) fluorescein in a buffer containing 100 mM TRIS pH 7.5, 500 mM sodium chloride, 0.1% (w/v) sodium azide, 1% (w/v) casein, 1 mM magnesium chloride, and 0.1 mM zinc. Typical working concentrations of the bihapten are 5 nM.

EXAMPLE 3

AxSYM® Progesterone Assay

Progesterone assays were performed on AxSYM® disposable cartridges by an AxSYM® instrument using a format similar to the IMx® assay in Example 2, with the following modifications.

42 microliters (42 µL) of a serum sample were mixed with 76 µL of an anti-progesterone/alkaline phosphatase conjugate reagent, and 68 µl of AxSYM® Progesterone Assay Buffer containing protein additives. The reaction mixture was incubated for 10 minutes at 31° C. 120 µl of the reaction was then added to 95 µl of a reagent which contains the equivalent of both the microparticle and bihapten reagents from Example 2. The incubation was continued for 9.2 rain at 31° C. One hundred thiri-y five microliters (135 µL) of the reaction mixture was transferred to the fiber matrix of an AxSYM® disposable cartridge. The complexes were then washed with AxSYM® Buffer, 50 µl of 4-methylumbelliferone phosphate was added, and the rate of 4 methylumbelliferone formation was quantified.

The anti-progesterone antibody/alkaline phosphatase conjugate reagent was prepared as described in Example 2 except that a recombinant alkaline phosphatase (Abbott) was used. The combined reagent contains microparticles and bihapten similar to those described in Example 2 in a buffer containing 150 mM TRIS pH 6.2, 200 mM sodium chloride, 18% (w/v) sucrose, 0.1% (w/v) sodium azide, 0.1% (v/v) Tween (™) 20, and 0.1 mg/mi mouse IgG.

EXAMPLE 4

Modulation of Recovery in the IMx® Progesterone Assay by Various cyclodextrins

The effects of cyclodextrins on the recovery of progesterone were examined in experiments summarized in FIG. 1. Progesterone was added to a final concentration of 4 ng/ml to serum and to various cyclodextrin solutions. The cyclodextrin solutions contained 0–10 mM of alpha, beta (3 lots, 2 vendors), or gamma cyclodextrin in 100 mM TRIS pH 8 (cyclodextrins are available from Sigma Chemical Co., St. Louis, Mo. and ICN, Irvine, Calif.). The apparent progesterone concentrations of these samples were determined using the progesterone assay on the IMx® instrument (Example 2). The observed concentration of progesterone in the serum sample (4.08 ng/ml) represents 100% recovery. The recovery of progesterone from the beta and gamma cyclodextrin samples varied from 20 to 190% (Recovery= observed/4.08×100%). Based on this experiment, a solution of 2.7 mM beta cyclodextrin or 1.3 mM gamma cyclodextrin would display a recovery equivalent to that observed with serum. Alpha cyclodextrin does not significantly affect progesterone recovery over the cyclodextrin concentrations examined in this study.

EXAMPLE 5

Figure 2:
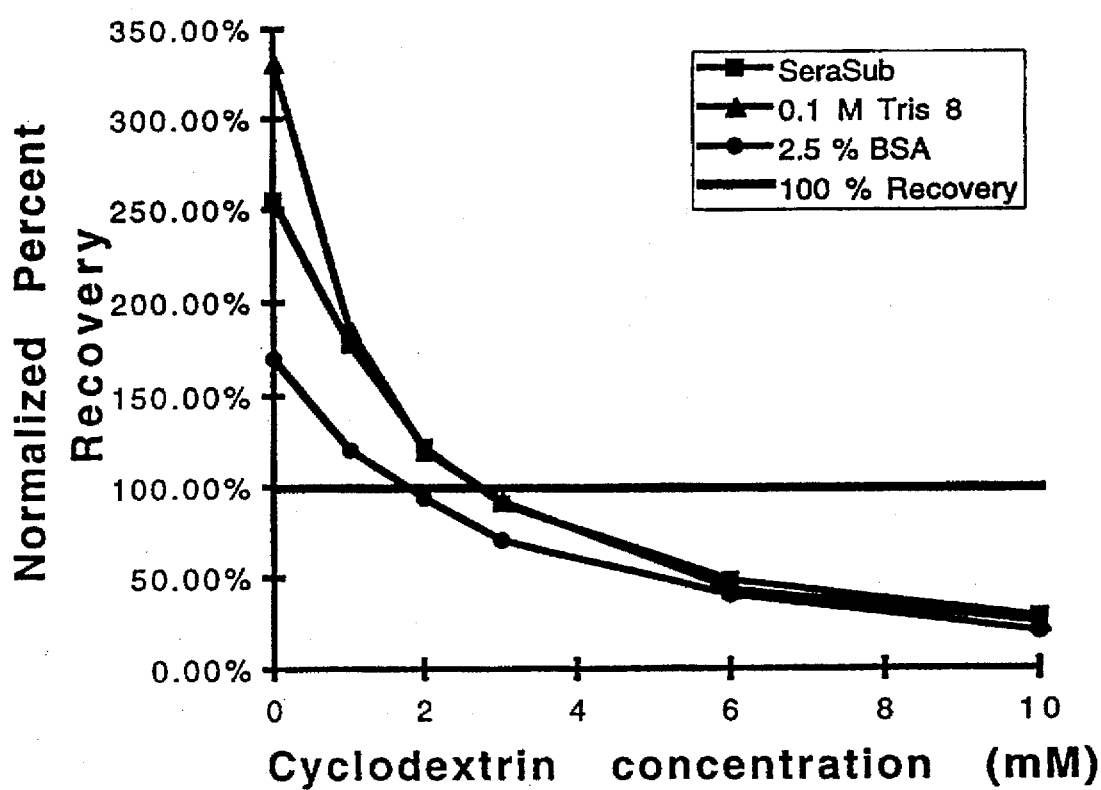
FIG. 2 is a graph of the Effects of Beta-cyclodextrin Recovery in Various Matrices.

Modulation of Recovery in Various Synthetic Matrices in the IMx®Progesterone Assay by βcyclodextrins The effects of cyclodextrins on the recovery of progesterone in various synthetic calibrator matrices were examined in experiments summarized in FIG. 2. Progesterone was added to a final concentration of 20 ng/ml to serum and to various synthetic calibrator matrices containing 0–10 mM beta cyclodextrin. The synthetic matrices included 100 mM TRIS pH 8, 100 mM TRIS pH 8 containing 2.5% (w/v) Bovine Serum Albumin (BSA) (available from Miles Pentex, Kankakee, Ill.), and SeraSub ™ (available from Creative Scientific Technology, Inc, Great Neck, N.Y.) The apparent progesterone concentrations of these samples were determined using the progesterone assay on the IMx® instrument (Example 2). An observed concentration of progesterone of 20 ng/ml represents 100% recovery. The recovery of progesterone from the cyclodextrin samples varied from 20 to 330% (Recovery=observed/20×100%). The cyclodextrin concentrations required to achieve 100% recovery are very similar for the matrices containing no protein (100 mM TRIS pH 8, SeraSub ™). Lower concentrations of cyclodextrin are needed for 100% recovery of progesterone in the presence of protein. The effects on the modulation of recovery of protein and cyclodextrin are additive. At high concentrations of protein (>12%) no cyclodextrin is needed for 100% recovery (data not shown).

EXAMPLE 6

Modulation of Recovery in the IMx® Estradiol Assay by β-cyclodextrins

Figure 3:
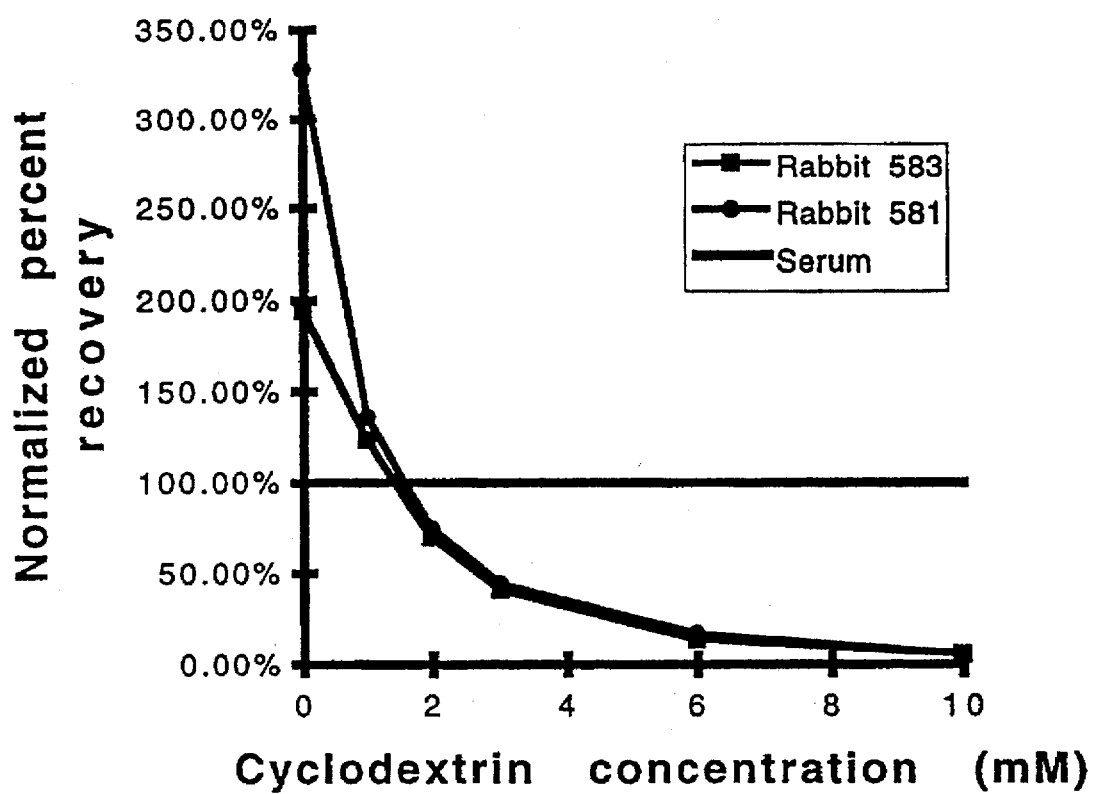
FIG. 3 is a graph of the Effects of Beta-cyclodextrin Concentration on Spike Recovery in the Estradiol Assay.

The effects of cyclodextrins on the recovery of estradiol were examined in experiments summarized in FIG. 3. Estradiol was added to a final concentration of 1 ng/ml to serum and to 100 mM TRIS pH 8 solutions containing 0–10 mM geta cyclodextrin. The apparent estradiol concentrations of these samples were determined using the IMx ® Estradiol Assay (Example 1). Two estradiol assay formats were examined in FIG. 3. The formats differed in the source of rabbit anti-estradiol used in the microparticle reagent (Rabbit 583 or Rabbit 581, Abbott). The recovery of estradiol from the cydodextrin samples varied from 5 to 330% (Recovery= observed (cyclodextrin)/observed (serum)×100%). Based on this experiment, a solution of approximately 1.5 to 1.75 mM beta cyclodextrin would display a recovery equivalent to that observed with serum.

EXAMPLE 7

Stabilization of Progesterone by β-cyclodextrin in the IMx® Progesterone Assay under Various Storage Conditions (56°, 45°, 37° C.)

Figure 4A:
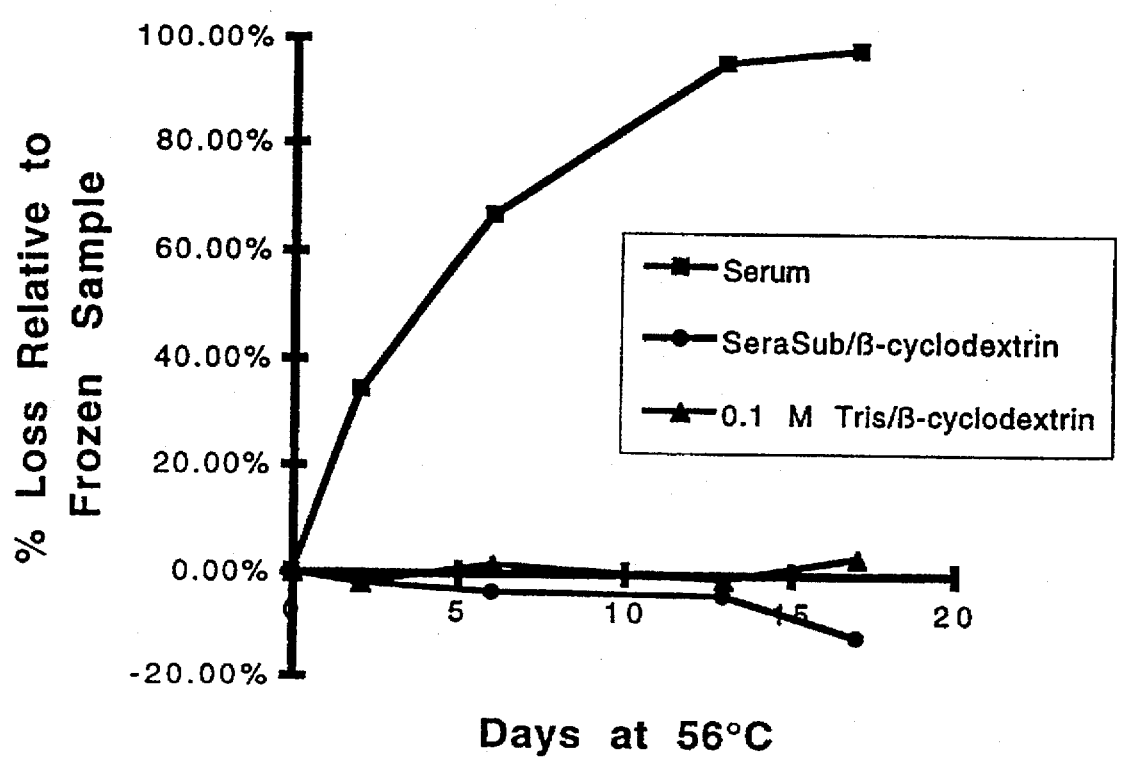
FIG. 4A is a graph of Stability of Progesterone at 56° C. in Serum and Various Matrices containing Beta-cyclodextrin.
Figure 4B:
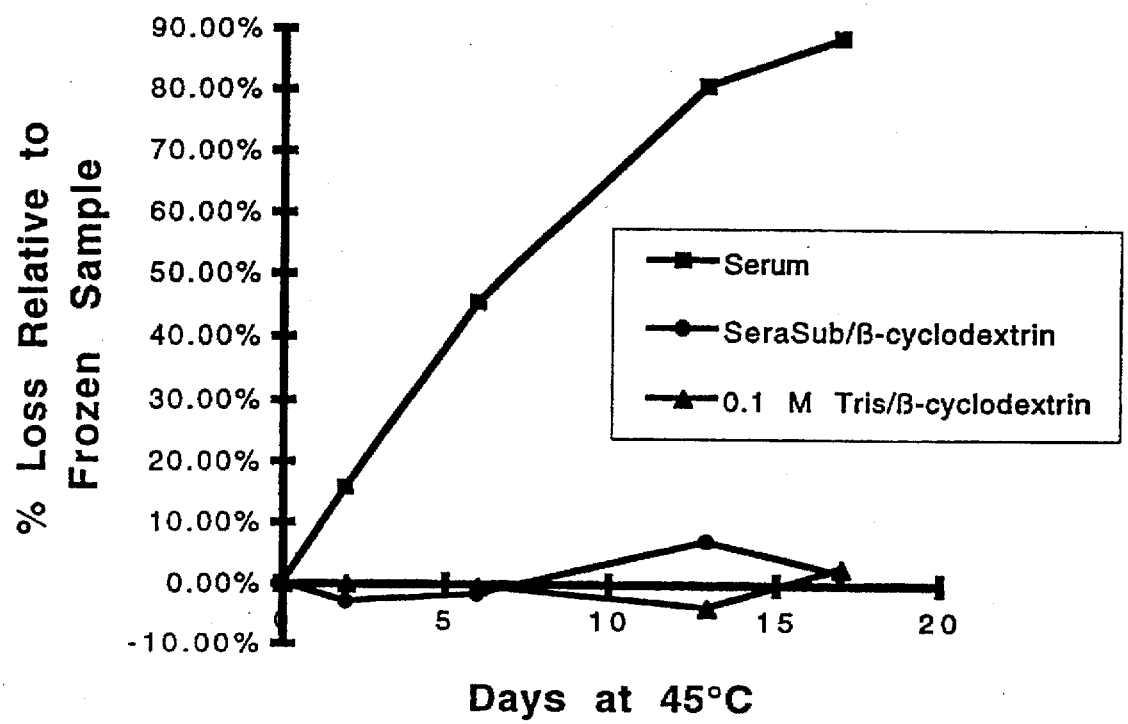
FIG. 4B is a graph of Stability of Progesterone at 45° C. in Serum and Various Matrices containing Beta-cyclodextrin.
Figure 4C:
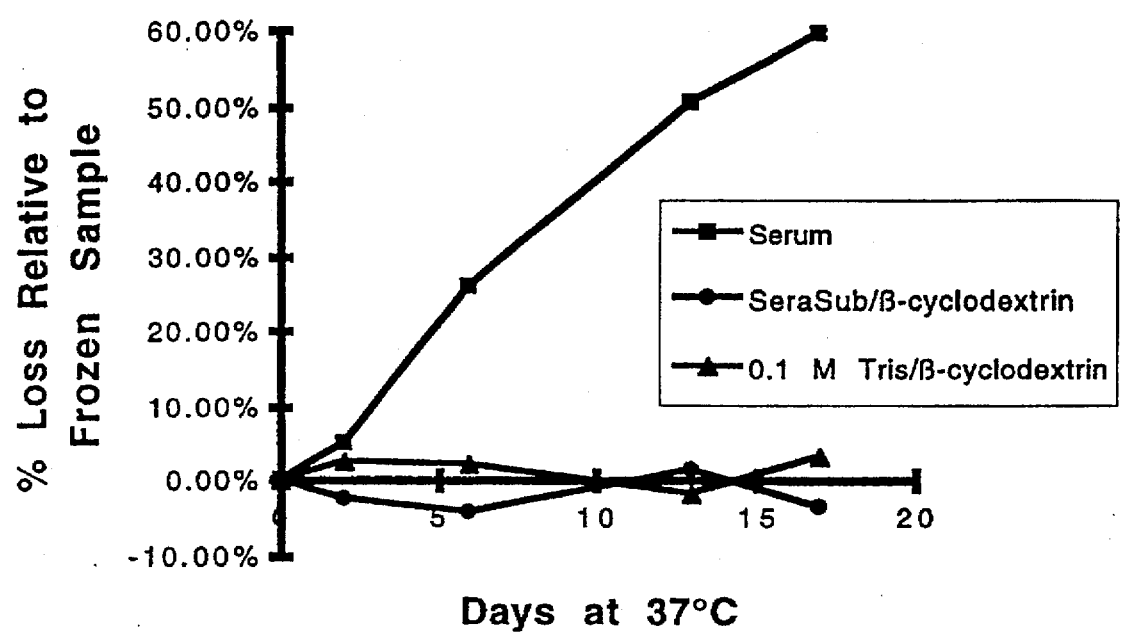
FIG. 4C is a graph of Stability of Progesterone at 37° C. in Serum and Various Matrices containing Beta-cyclodextrin.

The effects of beta cyclodextrin on the stability of progesterone were examined in experiments summarized in FIGS. 4A–C. Progesterone was added to a final concentration of 4 ng/ml to serum and to two synthetic calibrator matrices containing 2.5 mM beta cyclodextrin. The synthetic matrices were 100 mM TRIS pH 8 and SeraSub (™). These samples were aliquoted and incubated at 56°, 45°, 37°, or −20 ° C. for up to 17 days. At the designated time points the apparent progesterone concentrations of these samples were determined using the progesterone assay on the IMx® instrument (Example 2). For these experiments, a 0 ng/ml serum sample was included in the same assay run with the test aliquots. Concentrations were determined for each test sample by dividing the IMx ® instrument rate signal from the heat stressed or frozen sample by the signal from the 0 ng/ml sample and plotting the result on a displacement curve [rate (calibrator)/rate(0 ng/ml) vs concentration] previously developed for this assay. The per cent loss is determined by dividing the difference between the frozen and stressed conditions by the concentration obtained for the frozen aliquot. The results are displayed as percent loss. i.e., [(Frozen-Stressed)/Frozen]×100%.

The percent loss observed with the cyclodextrin containing samples is significantly less than that observed with the serum. At 56 ° C., 98% of the progesterone was lost from the serum sample while the TRIS and SeraSub ™ samples displayed virtually no loss.

The composition of the cyclodextrin samples was designed so that these samples would display a recovery equivalent to that of serum. In these experiments, the use, as a control, of a 0.1M TRIS or SeraSub ™ containing no cydodextrin was inappropriate because of issues relating to over-recovery, solubility and adherence of the steroid to the vessel wall under such a condition.

EXAMPLE 8

Figure 5A:
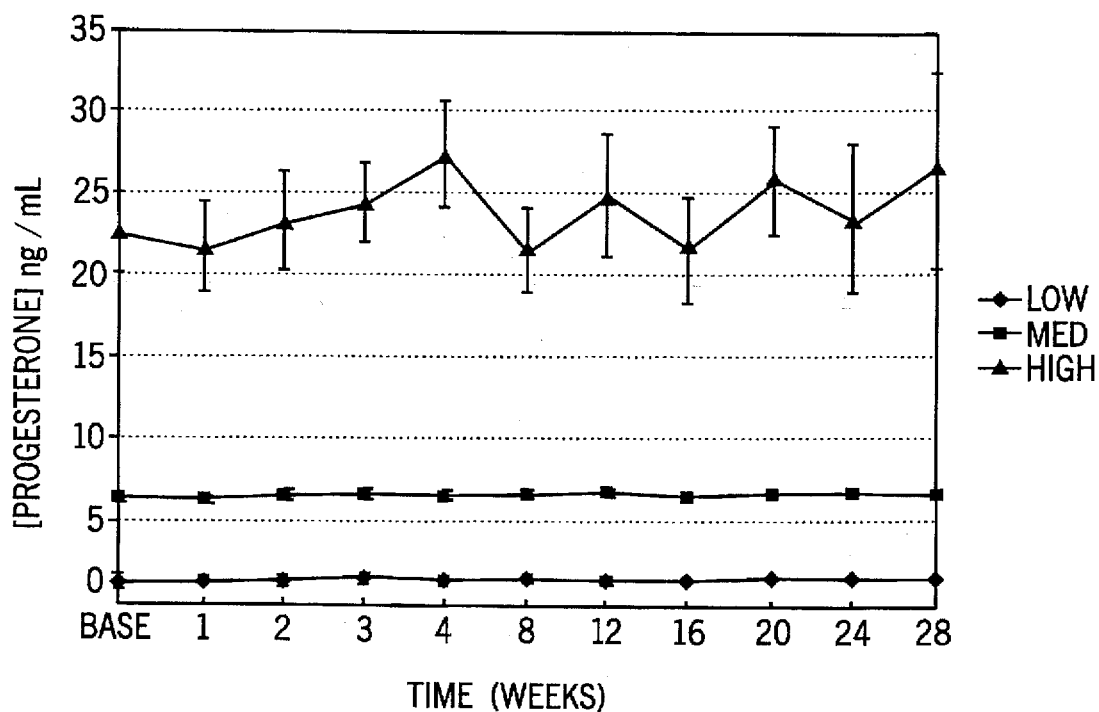
FIG. 5A is a graph of Progesterone Concentrations (0–35 ng/ml) of Frozen Panels determined using calibrators stored at 2°–8° C.
Figure 5B:
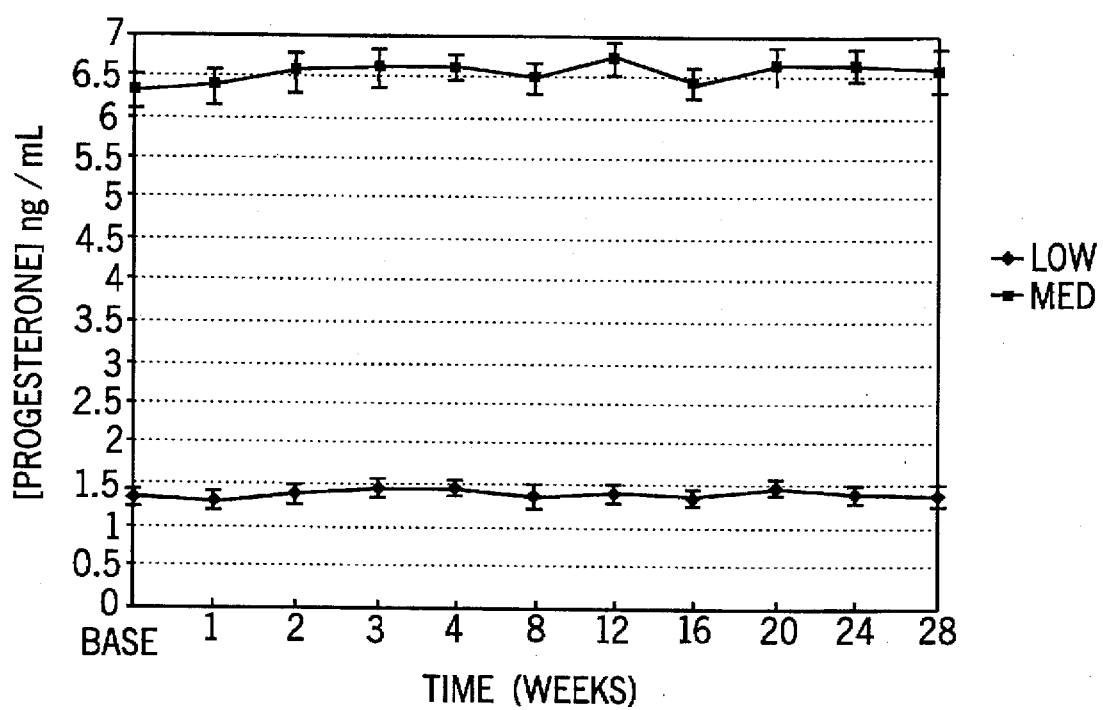
FIG. 5B is a graph of Progesterone Concentrations (0–7 ng/ml) of Frozen Panels determined using calibrators stored at 2°–8° C., extended y-axis.

Stabilization of Progesterone by β-cyclodextrin in the AxSYM® Progesterone Assay under Various Storage Conditions The effects of beta cyclodextrin on the long term stability of progesterone were examined in experiments summarized in FIGS. 5A and B. Beta cyclodextrin calibrators were prepared in 100 mM TRIS pH 8 at 0, 0.7, 2.0, 7.0, 20, and 40 ng/ml and stored at 2°–8° C. Serum based panels were prepared at approximately 1.3 (Low), 6 (Medium), and 22 (High) ng/ml and then frozen, a condition in which progesterone is stable. At the designated time points the progesterone concentrations of these panels were determined with the stored calibrators using the AxSYM® Progesterone Assay (Example 3). The data in FIGS. 5A and 5B indicate that the panel concentrations are remaining constant over time. If there was a loss of progesterone in the calibrators stored at 2°–8° C., the apparent concentrations of progesterone in the frozen panels would have trended upward. (Note, the calibrators used for the week 16 time point were stored frozen. The calibrators used for all of the ohher time points were stored at 2°–8° C.) (Error bars represent two standard deviations, n=18 for each time point)

Figure 6:
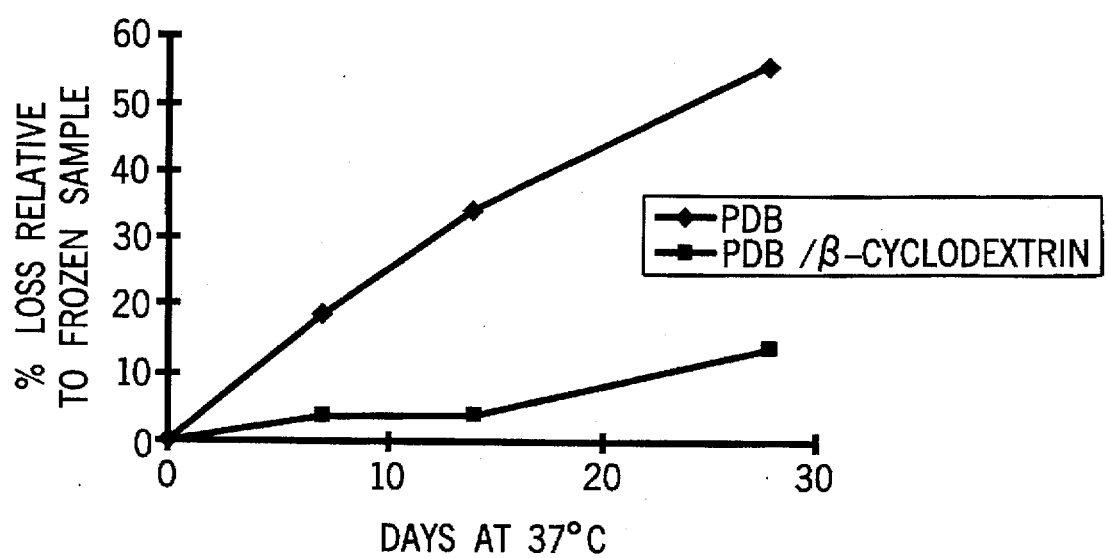
FIG. 6 is a graph of Stability of Progesterone at 37° C. in Plasma Diagnostic Base, with and without Beta-cyclodextrin.

EXAMPLE 9: Stabilization of Progesterone by β-cyclodextrin in the IMx® Progesterone Assay at 37° C. in Matrices Containing Protein The effects of β-cyclodextrin on the stability of progesterone in protein containing matrices were examined in experiments summarized in FIG. 6. Progesterone was added to a final concentration of 4 ng/ml to charcoal-stripped Plasma Diagnostic Base (PDB, Intergen Co, New York) alone, and to charcoal-stripped PDB containing 1.5 mM β-cyclodextrin. In this second matrix, PDB was diluted slightly to compensate for the effect of β-cyclodextrin on the recovery of progesterone. These samples were aliquoted and incubated at 37°, or −20 ° C. for up to 28 days. At the designated time points the apparent progesterone concentrations of these samples were determined using the progesterone assay on the IMx® instrument (Example 2). The method used to calculate the concentration and % loss of progesterone was the same as in Example 7. The % loss of progesterone is significantly less in PDB containing β-cyclodextrin than in PDB alone. Over 28 days of incubation at 37° C. only 13% of the original concentralion of progesterone is lost, as opposed to 56% in PDB containing no β-cyclodextrin. This example demonstrates that cyclodextrins, and in particular β-cyclodextrin, can be utilized to stabilize steroid formulations in protein-containing media.

The embodiments described and the alternative embodiments presented are intended as examples rather than limitations. Thus, the description of the invention is not intended to limit the invention to the particular embodiments disclosed, but it is intended to encompass all equivalents and subject matter within the spirit and scope of the invention as described above and as set in the following claims.

We claim:

1. A control composition for asteroid immunoassay comprising asteroid and an amount of a cyclodextrin effective to achieve a level of steroid recovery that mimics the steroid recovery of human serum in an aqueous medium.

2. The control composition of claim 1 wherein the cyclodextrin is selected from the group consisting of Beta, Gamma, and modified Beta-cyclodextrin.

3. The control composition of claim 1 wherein the aaueous medium is a substantially protein-free aqueous matrix.

4. The control composition of claim 1 wherein the cyclodextrin is β-cyclodextrin.

5. The control composition of claim 1 wherein the steroid is estradiol or progesterone.

6. The control composition of claim 5 wherein the steroid is estradiol.

7. The control composition of claim 3 wherein the aqueous matrix is substantially free of fibrinogen.

8. The control composition of claim 3 wherein the aqueous matrix is other than plasma.

9. The control composition of claim 1 further comprising a protein selected from the group consisting of human serum and bovine serum albumin.

10. The control composition of claim 9 wherein said human serum is charcoal stripped.

11. The control composition of claim 1 wherein the steroid has a concentration of from about $2.5 \times 10^{-11}$ to about $1.0 \times 10^{-7}$ g/m L.

12. The control composition of claim 2 wherein the concentration of the cyclodextrin is from about 2.0 mM to about 3.0 mM.

13. The control composition of claim 12 wherein the steroid is progesterone or estradiol.

14. The control composition of claim 1 wherein the level of steroid recovery is about 100%.

15. A calibrator composition for use in asteroid immunoassay comprising:

(1) a steroid; and (2) an amount of a cyclodextrin effective to achieve a level of steroid recovery that mimics the steroid recovery of human serum in an aaueous medium.

16. The calibrator composition of claim 15 wherein the cyclodextrin is selected from the group consisting of β-, Gamma-, and modified β-cyclodextrin.

17. The calibrator composition of claim 16 wherein the cyclodextrin is β-cyclodextrin.

18. The calibrator composition of claim 15 further comprising a protein selected from the group consisting of human serum and bovine serum albumin.

19. The calibrator composition of claim 18 wherein said human serum is charcoal stripped.

20. The calibrator composition of claim 15 wherein the steroid has a concentration of from about $2.5 \times 10^{-11}$ to about $1.0 \times 10^{-7}$ g/mL and the cyclodextrin has a concentration of from about 2.0 mM to about 3.0 mM.

* * * * *